(12) United States Patent
Tonomura et al.

(10) Patent No.: US 6,518,447 B2
(45) Date of Patent: Feb. 11, 2003

(54) THEXYLCHLOROSILANES AND MAKING PROCESS

(75) Inventors: Yoichi Tonomura, Niigata-ken (JP); Tohru Kubota, Niigata-ken (JP); Yasufumi Kubota, Niigata-ken (JP)

(73) Assignee: Shin-Etsu Chemical Co., Ltd., Tokyo (JP)

(*) Notice: Subject to any disclaimer, the term of this patent is extended or adjusted under 35 U.S.C. 154(b) by 0 days.

(21) Appl. No.: 09/985,528

(22) Filed: Nov. 5, 2001

(65) Prior Publication Data

US 2002/0055647 A1 May 9, 2002

(30) Foreign Application Priority Data

Nov. 6, 2000 (JP) ........................................ 2000-337366

(51) Int. Cl.$^7$ .................................................... C07F 7/08
(52) U.S. Cl. ........................ 556/465; 556/438; 556/440; 556/442
(58) Field of Search ............................... 552/465, 438, 552/440, 442

(56) References Cited

U.S. PATENT DOCUMENTS 4,695,643 A * 9/1987 Oertle et al. ............ 556/465 X

* cited by examiner

*Primary Examiner*—Paul F. Shaver
(74) *Attorney, Agent, or Firm*—Millen, White, Zelano & Branigan, P.C.

(57) ABSTRACT

Chlorosilane compounds having a thexyl group which is a bulky substituent group are novel. The compounds are useful silylating agents because stable silylated products are obtained due to the bulky substituent group.

9 Claims, 2 Drawing Sheets

THEXYLCHLOROSILANES AND MAKING PROCESS

This invention relates to novel chlorosilane compounds having a thexyl group, and a process for preparing the same. These novel compounds are useful as a silylating agent because their bulky substituent group improves the stability of silylated products.

BACKGROUND OF THE INVENTION

Silylating agents are used with alcohols and carboxylic acids for the purpose of protecting active hydrogen-bearing substituent groups thereon. The silylated compounds are useful in a variety of applications, typically as intermediates to pharmaceutical drugs and pesticides.

Most common among the silylating agents are compounds having a silicon-chlorine bond within their molecule, known as chlorosilane compounds. Silylation is effected by reacting the chlorosilane compounds with alcohols or carboxylic acids. The silylating agents of the chlorosilane type currently used in the art include trimethylchloro-silane, triethylchlorosilane, t-butyldimethylchlorosilane and triisopropylchlorosilane. However, products silylated with these silylating agents have insufficient steric bulkiness so that they are prone to hydrolysis and unsatisfactorily stable. There is a need for a silylating agent having a bulky substituent group to ensure that the product silylated therewith becomes more stable.

SUMMARY OF THE INVENTION

An object of the invention is to provide a chlorosilane compound having a bulky substituent group useful as a silylating agent capable of affording more stable silylated products. Another object is to provide a process for preparing the chlorosilane compound.

It has been found that a thexylchlorosilane compound having the following general formula (1):

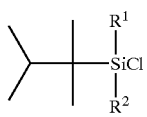

(1)

wherein each of $R^1$ and $R^2$ is a monovalent branched hydrocarbon group of 3 to 10 carbon atoms having a hydrocarbon group at the same or different α- or β-position or a monovalent cyclic hydrocarbon group of 3 to 10 carbon atoms can be prepared by reacting 2,3-dimethyl-2-butene with a hydrogenchlorosilane compound having the following general formula (2):

$$HSiR^1R^2Cl \quad (2)$$

wherein $R^1$ and $R^2$ are as defined above, in the presence of aluminum chloride. This chlorosilane compound having a thexyl group, simply referred to as thexylchlorosilane compound, is novel. When used as a silylating agent, it affords a more stable silylated product.

Accordingly, the invention provides a thexylchloro-silane compound of the formula (1). The invention also provides a process for preparing the thexylchlorosilane compound of the formula (1) by reacting 2,3-dimethyl-2-butene with a hydrogenchlorosilane compound of the formula (2) in the presence of aluminum chloride.

DESCRIPTION OF THE PREFERRED EMBODIMENT

Figure 1:
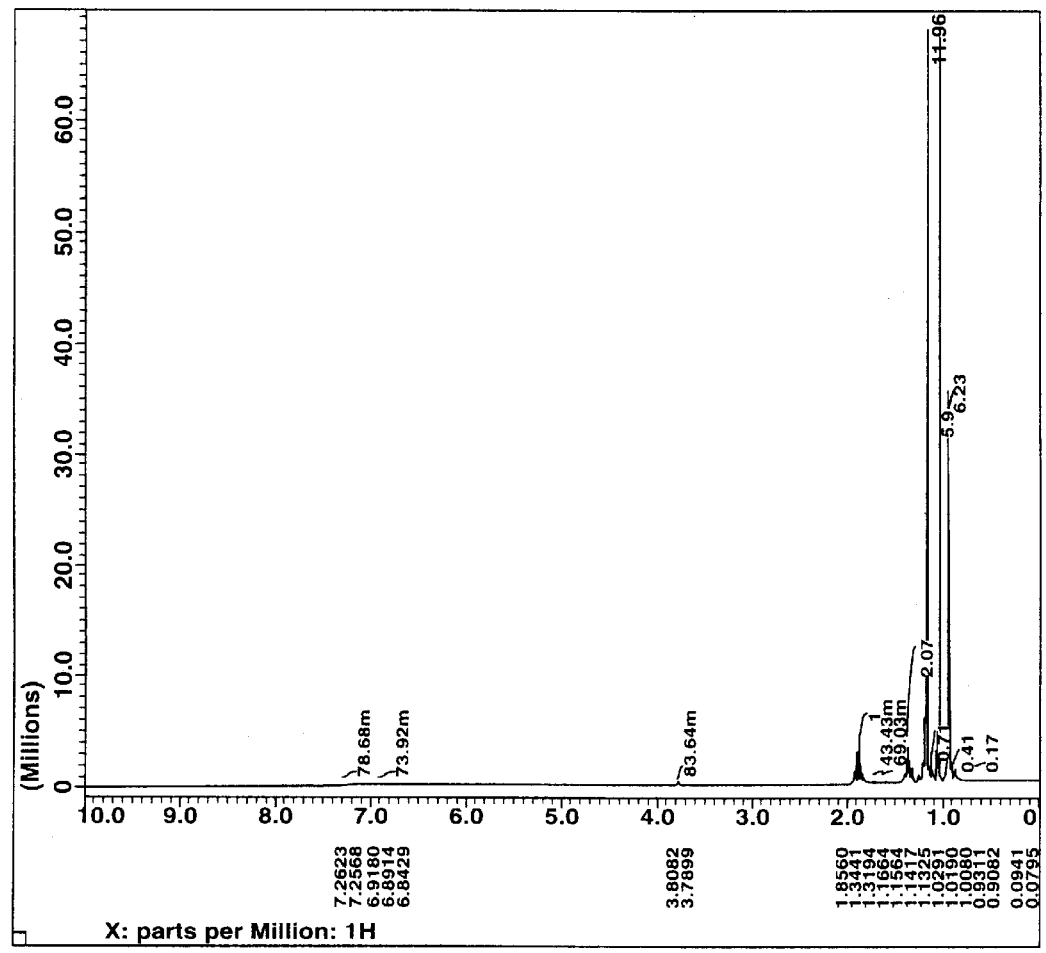
FIGS. 1 and 2 are $^1$H NMR and IR spectra of thexyldiisopropylchlorosilane obtained in Example 1, respectively.

The thexylchlorosilane compound according to the invention has the following general formula (1).

(1)

Herein each of $R^1$ and $R^2$ is a monovalent branched hydrocarbon group of 3 to 10 carbon atoms having a hydrocarbon group at the same or different α- or β-position or a monovalent cyclic hydrocarbon group of 3 to 10 carbon atoms.

The branched and cyclic hydrocarbon groups of 3 to 10 carbon atoms represented by $R^1$ and $R^2$ are preferably branched alkyl groups and cycloalkyl groups, for example, isopropyl, isobutyl, s-butyl, 1-methylbutyl, 1-ethylpropyl, 2-ethylhexyl, cyclopentyl and cyclohexyl.

Illustrative, non-limiting examples of the thexylchlorosilane compound of formula (1) include thexyldiisopropylchlorosilane, thexyldiisobutylchlorosilane, thexyldi-s-butylchlorosilane, thexyldi(1-methylbutyl)chloro-silane, thexyldi(1-ethylpropyl)chlorosilane, thexyldi(2-ethylhexyl) chlorosilane, thexyldicyclopentylchlorosilane, thexyldicyclohexylchlorosilane, thexylisopropylisobutyl-chlorosilane, and thexylisopropyl-s-butylchlorosilane. Of these, thexyldiisopropylchlorosilane and thexyldiisobutyl-chlorosilane are preferred because of ease of preparation and usefulness of silylated products.

The thexylchlorosilane compound of the formula (1) according to the invention is prepared, for example, by reacting 2,3-dimethyl-2-butene with a hydrogenchlorosilane compound of the following general formula (2) in the presence of aluminum chloride.

$$HSiR^1R^2Cl \quad (2)$$

Herein $R^1$ and $R^2$ are as defined above.

Illustrative, non-limiting examples of the hydrogenchlorosilane compound of formula (2) include diisopropylchlorosilane, diisobutylchlorosilane, di-s-butylchlorosilane, di(1-methylbutyl)chlorosilane, di(1-ethylpropyl)chlorosilane, di(2-ethylhexyl)chlorosilane, dicyclopentylchlorosilane, dicyclohexylchlorosilane, isopropylisobutylchlorosilane, and isopropyl-s-butylchlorosilane.

The proportion of 2,3-dimethyl-2-butene and the hydrogenchlorosilane compound of formula (2) is not critical although it is preferred for reactivity and productivity that 0.5 to 2.0 mol, and especially 0.8 to 1.2 mol of the hydrogenchlorosilane compound be used per mol of 2,3-dimethyl-2-butene.

The amount of aluminum chloride added as the catalyst in the above reaction is not critical although it is preferred for reactivity and productivity that 0.001 to 0.5 mol, and especially 0.01 to 0.2 mol of aluminum chloride be used per mol of 2,3-dimethyl-2-butene. Less than 0.001 mol of aluminum chloride may fail to exert the desired catalysis whereas more than 0.5 mol of aluminum chloride may fail to achieve the reaction promoting effect for that catalyst amount.

Other reaction conditions are not critical although the reaction is preferably effected at a temperature of −20° C. to 150° C., especially 0° C. to 100° C. and atmospheric pressure or sufficient pressure.

It is noted that the reaction proceeds even in a solventless system although a solvent is optionally used. Examples of the solvent which can be used herein include aliphatic hydrocarbon solvents such as pentane, hexane, isooctane, and cyclohexane, aprotic polar solvents such as acetonitrile, and chlorinated hydrocarbon solvents such as dichloromethane and chloroform.

The above reaction may be performed in various ways, for example, a way of adding aluminum chloride to a mixture of 2,3-dimethyl-2-butene and the hydrogenchlorosilane compound, a way of adding the hydrogenchlorosilane compound to a mixture of 2,3-dimethyl-2-butene and aluminum chloride, a way of adding 2,3-dimethyl-2-butene to a mixture of the hydrogenchlorosilane compound and aluminum chloride, and a way of adding both 2,3-dimethyl-2-butene and the hydrogenchlorosilane compound to a mixture of aluminum chloride and a solvent. After the completion of reaction, the end compound can be recovered in a conventional manner.

EXAMPLE

Examples of the invention are given below by way of illustration and not by way of limitation.

Example 1

Thexyldiisopropylchlorosilane

A flask equipped with a stirrer, reflux condenser, dropping funnel and thermometer was charged with 30.1 g (0.2 mol) of diisopropylchlorosilane and 2.7 g (0.02 mol) of aluminum chloride and heated at 50° C. Once the internal temperature became constant, 16.8 g (0.2 mol) of 2,3-dimethyl-2-butene was added dropwise over one hour. After the completion of dropwise addition, the reaction solution was stirred for one hour at 50° C. The aluminum chloride was deactivated by adding 4.3 g (0.04 mol) of anisole. The reaction solution was distilled, collecting 28.3 g of a boiling point 79° C./133 Pa fraction.

This fraction was analyzed by mass spectroscopy, $^1$H-NMR and IR spectroscopy, with the results shown below.

Figure 2:
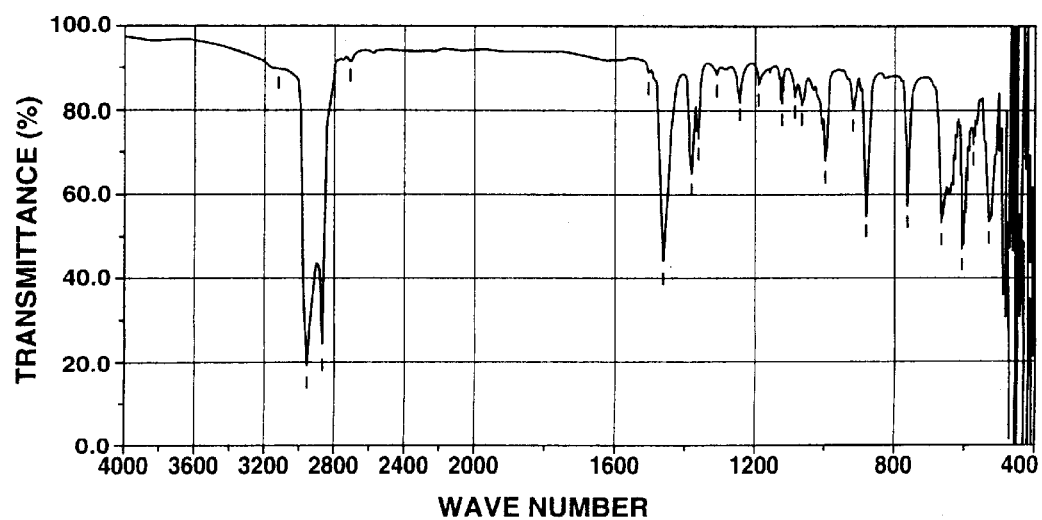

Mass spectrum: m/s 234 (M+), 149, 121, 93, 84, 43; $^1$H-NMR spectrum (heavy chloroform solvent); FIG. 1; IR spectrum; FIG. 2.

From these analytical results, the compound obtained was identified to be thexyldiisopropylchlorosilane (yield 60%).

Example 2

Thexyldiisobutylchlorosilane

A flask equipped with a stirrer, reflux condenser, dropping funnel and thermometer was charged with 35.8 g (0.2 mol) of diisobutylchlorosilane and 2.7 g (0.02 mol) of aluminum chloride and heated at 50° C. Once the internal temperature became constant, 16.8 g (0.2 mol) of 2,3-dimethyl-2-butene was added dropwise over one hour. After the completion of dropwise addition, the reaction solution was stirred for one hour at 50° C. The aluminum chloride was deactivated by adding 4.3 g (0.04 mol) of anisole. The reaction solution was distilled, collecting 32.5 g of a boiling point 83° C./133 Pa fraction.

This fraction was analyzed by mass spectroscopy, $^1$H-NMR and IR spectroscopy, with the results shown below.

Figure 3:
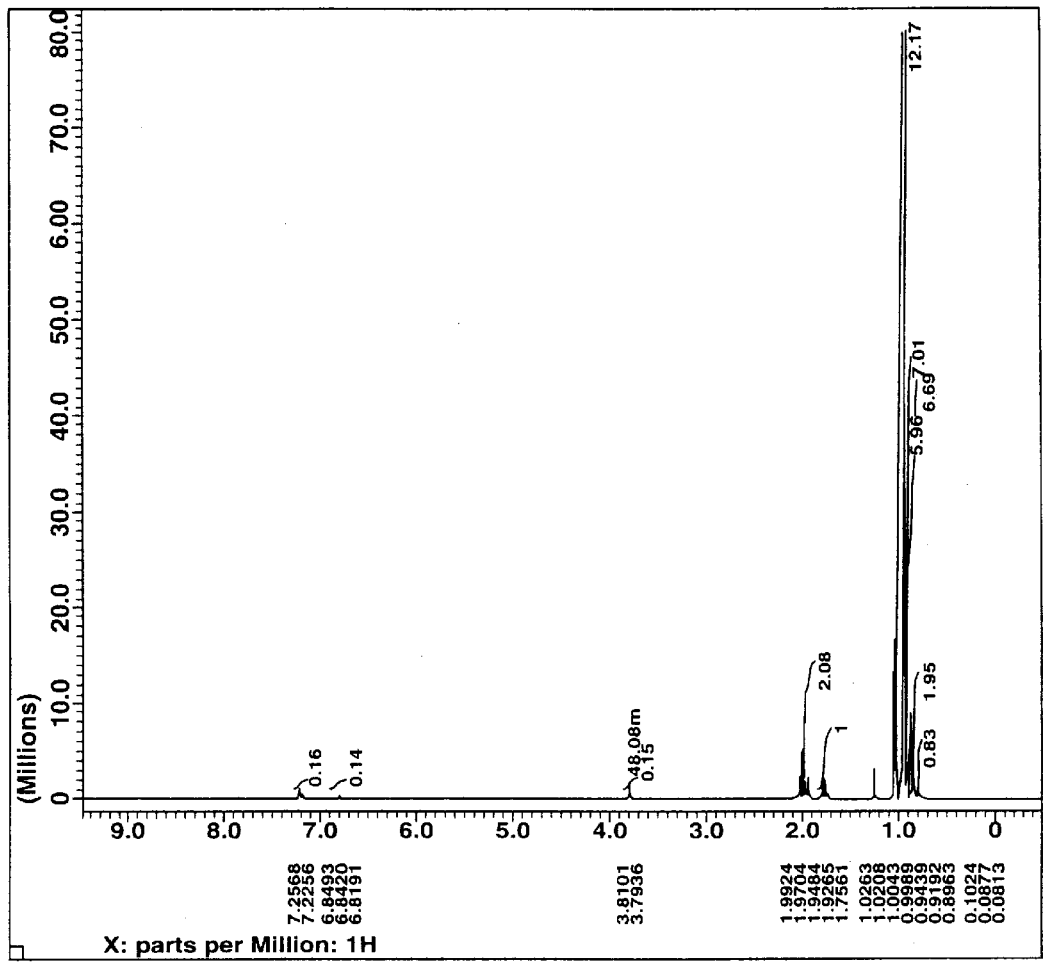
FIGS. 3 and 4 are $^1$H NMR and IR spectra of thexyldiisobutylchlorosilane obtained in Example 2, respectively.
Figure 4:
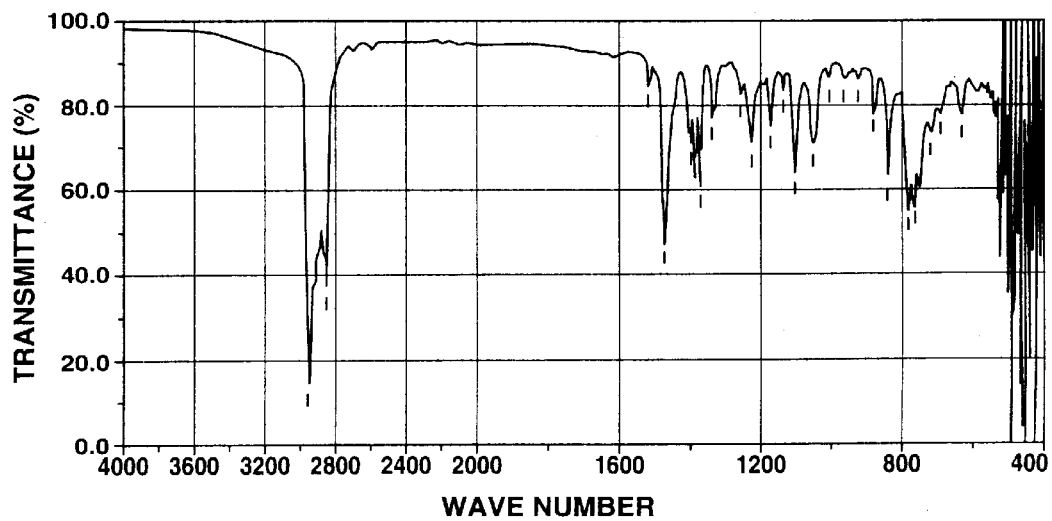

Mass spectrum: m/s 262 (M+), 177, 135, 95, 84, 43; $^1$H-NMR spectrum (heavy chloroform solvent); FIG. 3; IR spectrum; FIG. 4.

From these analytical results, the compound obtained was identified to be thexyldiisobutylchlorosilane (yield 62%).

There have been described thexylchlorosilane compounds or chlorosilane compounds having a thexyl group which is a bulky substituent group. The compounds are useful silylating agents because stable silylated products are obtained due to the bulky substituent group.

Japanese Patent Application No. 2000-337366 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A thexylchlorosilane compound having the following general formula (1):

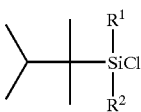

(1)

wherein each of $R^1$ and $R^2$ is a monovalent branched hydrocarbon group of 3 to 10 carbon atoms having a hydrocarbon group at the same or different α- or β-position or a monovalent cyclic hydrocarbon group of 3 to 10 carbon atoms.

2. The thexylchlorosilane compound of claim 1 which is thexyldiisopropylchlorosilane or thexyldiisobutylchlorosilane.

3. A process for preparing the thexylchlorosilane compound of the general formula (1) according to claim 1, said process comprising the step of reacting 2,3-dimethyl-2-butene with a hydrogenchlorosilane compound having the following general formula (2):

$$HSiR^1R^2Cl \qquad (2)$$

wherein $R^1$ and $R^2$ are as defined above, in the presence of aluminum chloride.

4. A thexylchlorosilane compound according to claim 1, wherein $R^1$ and $R^2$ are, each independently, isopropyl, isobutyl, s-butyl, 1-methylbutyl, 1-ethylpropyl, 2-ethylhexyl, cyclopentyl or cyclohexyl.

5. A thexylchlorosilane compound according to claim 1, which is thexyldiisopropylchlorosilane, thexyldiisobutylchlorosilane, thexyldi-s-butylchlorosilane, thexyldi(1-methylbutyl)chlorosilane, thexyldi(1-ethylpropyl)chlorosilane, thexyldi(2-ethylhexyl)chlorosilane, thexyldicyclopentylchlorosilane, thexyldicyclohexylchlorosilane, thexylisopropylisobutylchlorosilane, or thexylisopropyl-s-butylchlorosilane.

6. A method of silylating a compound comprising derivatizing said compound with a compound according to claim 1.

7. A method of silylating a comprising derivatizing said compound with a compound according to claim 2.

8. A silylated compound prepared by the method of claim 6.

9. A silylated compound prepared by the method of claim 7.

* * * * *